United States Patent
Mostafavi

(10) Patent No.: US 9,517,036 B2
(45) Date of Patent: Dec. 13, 2016

(54) RADIATION IMAGING USING VERY SLOW ROTATIONAL TECHNIQUE

(75) Inventor: Hassan Mostafavi, Los Altos, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 49 days.

(21) Appl. No.: 13/589,514

(22) Filed: Aug. 20, 2012

(65) Prior Publication Data

US 2014/0050297 A1 Feb. 20, 2014

(51) Int. Cl.
*A61B 6/03* (2006.01)
*A61B 6/02* (2006.01)
*A61B 6/00* (2006.01)

(52) U.S. Cl.
CPC .............. *A61B 6/035* (2013.01); *A61B 6/025* (2013.01); *A61B 6/486* (2013.01); *A61B 6/5288* (2013.01); *A61B 6/584* (2013.01); *A61B 6/032* (2013.01); *A61B 6/4441* (2013.01); *A61B 6/5235* (2013.01)

(58) Field of Classification Search
CPC ....... A61B 6/025; A61B 6/5264; A61B 6/527; A61B 6/541; A61B 6/035; A61B 6/032; A61B 6/4441; A61B 6/486; A61B 6/5288; A61B 6/027; A61B 6/5235; A61B 6/584
USPC ........................................ 378/8, 19; 600/428
See application file for complete search history.

(56) References Cited

U.S. PATENT DOCUMENTS

| | | | | |
|---|---|---|---|---|
| 4,662,379 A | * | 5/1987 | Macovski | 600/428 |
| 6,324,254 B1 | * | 11/2001 | Pflaum | A61B 5/02007 378/8 |
| 6,862,337 B2 | * | 3/2005 | Claus | A61B 6/025 378/22 |
| 7,127,028 B2 | * | 10/2006 | Sendai | A61B 6/025 378/155 |
| 8,582,719 B2 | * | 11/2013 | Bani-Hashemi | A61B 6/025 378/21 |
| 2005/0135664 A1 | * | 6/2005 | Kaufhold | G06T 11/006 382/131 |
| 2005/0175141 A1 | * | 8/2005 | Bruder | A61B 6/032 378/8 |
| 2006/0133564 A1 | * | 6/2006 | Langan | G01N 23/046 378/8 |

(Continued)

OTHER PUBLICATIONS

Extended European Search Report dated Jan. 22, 2014 for EP Patent Application No. 13180911.3 (6 pages).

*Primary Examiner* — Wyatt Stoffa
(74) *Attorney, Agent, or Firm* — Vista IP Law Group, LLP

(57) ABSTRACT

An imaging system includes a radiation source, a positioner configured to rotate the radiation source along an arc path at a rate less than 0.5 degree/sec, an imager in operative position relative to the radiation source, wherein the radiation source and the imager are configured to obtain a plurality of images while the radiation source is at different positions along the arc path, and a processor configured to determine a digital tomosynthesis image using a subset of the plurality of images. An imaging method includes generating a control signal to control a positioner to rotate a radiation source through an arc path at a rate less than 0.5 degree/sec, obtaining a plurality of images that are generated using radiation from the radiation source while the radiation source is at different positions along the arc path, and determining a digital tomosynthesis image using a subset of the plurality of images.

46 Claims, 9 Drawing Sheets

(56) References Cited

U.S. PATENT DOCUMENTS

| | | | |
|---|---|---|---|
| 2007/0025509 A1* | 2/2007 | Pang | A61B 6/025 378/65 |
| 2007/0100227 A1* | 5/2007 | Schonborn | A61B 6/4441 600/407 |
| 2007/0237290 A1* | 10/2007 | Mostafavi | A61B 6/025 378/21 |
| 2008/0056547 A1* | 3/2008 | Kokubun | A61B 6/032 382/128 |
| 2009/0076369 A1* | 3/2009 | Mistretta | A61B 6/482 600/407 |
| 2009/0092225 A1* | 4/2009 | Boese | A61B 6/025 378/19 |
| 2009/0135995 A1* | 5/2009 | Eberhard | A61B 6/025 378/19 |
| 2009/0225933 A1* | 9/2009 | Shao | A61B 6/032 378/15 |
| 2010/0067739 A1* | 3/2010 | Mostafavi | G06T 7/2086 382/103 |
| 2010/0098221 A1* | 4/2010 | Diez | 378/205 |
| 2011/0002441 A1* | 1/2011 | Vogtmeier | A61B 6/025 378/21 |
| 2011/0002442 A1* | 1/2011 | Thran | H01J 35/065 378/22 |
| 2011/0142316 A1* | 6/2011 | Wang | G06T 11/006 382/131 |
| 2011/0235774 A1* | 9/2011 | Dolazza | A61B 6/502 378/11 |
| 2011/0268246 A1* | 11/2011 | Dafni | A61B 6/032 378/8 |
| 2012/0123251 A1* | 5/2012 | Erbel | A61B 6/025 600/424 |
| 2012/0307964 A1* | 12/2012 | Hall | A61B 6/03 378/8 |
| 2013/0083889 A1 | 4/2013 | Stancanello | |
| 2013/0294573 A1* | 11/2013 | Dolazza | A61B 6/502 378/11 |
| 2014/0192952 A1* | 7/2014 | Keall | A61B 6/4085 378/8 |
| 2015/0025370 A1* | 1/2015 | Neukirchen | A61B 6/032 600/425 |

* cited by examiner

RADIATION IMAGING USING VERY SLOW ROTATIONAL TECHNIQUE

FIELD

This application relates to systems and methods for obtaining images of a patient.

BACKGROUND

Radiation therapy has been employed to treat tumorous tissue. In radiation therapy, a high energy beam is applied from an external source towards the patient. The external source, which may be rotating (as in the case for arc therapy), produces a collimated beam of radiation that is directed into the patient to the target site. The dose and placement of the dose must be accurately controlled to ensure that the tumor receives sufficient radiation, and that damage to the surrounding healthy tissue is minimized.

Sometimes, before a radiation therapy is performed, the target region of the patient is imaged using a CT system for diagnostic purpose, or for treatment planning. For the case in which the target region moves in a periodic motion (e.g., due to breathing), the CT system may be used to determine volumetric images of the target when the target is at different breathing states, so that the volumetric images may be played back as a video stream. One such imaging technique is known as 4D cone beam CT (CBCT). For such purpose, projection images of the target when the target is at different breathing states are acquired, and a breathing monitoring device is used to determine breathing states of the patient as the CT system acquires the projection images. After the imaging session, the projection images are then sorted according to the recorded breathing states of the patient when the corresponding projection images are acquired. The breathing monitoring device is required to track the breathing states accurately. The tracked breathing states cannot be too coarse (e.g., they cannot merely indicate whether the patient is at an inhale state or an exhale state) because otherwise, the resulting video stream would be too coarse for diagnostic and treatment planning purposes.

However, Applicant of the subject application has determined that 4D CBCT imaging is time consuming and the large number of projections may potentially expose the patient to excessive x-ray imaging does. Accordingly, instead of generating a video using a sequence of CT images, it may be desirable to generate the video using a sequence of digital tomosynthesis images (4D DTS).

Digital tomosynthesis image is an image that is reconstructed using projection images, wherein the number of projection images involved may be less than those for a CT image. However, existing techniques for obtaining projection images for reconstruction of a digital tomosynthesis image may not be desirable for 4D DTS. This is because existing imaging techniques are designed to perform rapid imaging in the interest of reducing the duration of an imaging session. However, rapid imaging may result in projections within each phase bin (i.e., the projection images that are used to reconstruct the tomosynthesis image for a certain phase or phase range) having non-uniform angular distribution, which may in turn degrades the geometric fidelity and depth resolution of the resulting digital tomosynthesis image.

SUMMARY

In accordance with some embodiments, a novel imaging method for enhancing visualization and/or successful tracking of a target that moves pseudo-periodically (e.g., as with respiration or heart beat) and that is obscured by overlaying structures is provided.

In accordance with some embodiments, an imaging system includes a radiation source, a positioner configured to rotate the radiation source along an arc path at a rate that is equal to or less than $\alpha/T$, an imager in operative (e.g., opposite) position relative to the radiation source, wherein the radiation source and the imager are configured to obtain a plurality of images while the radiation source is at different positions along the arc path, and a processor configured to determine a digital tomosynthesis image using a subset of the plurality of images, where $\alpha$ is an angular spacing between a subset of the images that belongs to a same bin, and T is a period of a physiological motion.

In accordance with other embodiments, an imaging method includes generating a control signal to control a positioner to rotate a radiation source through an arc path at a rate that equal to or less than $\alpha/T$, obtaining a plurality of images that are generated using radiation from the radiation source while the radiation source is at different positions along the arc path, and determining a digital tomosynthesis image using a subset of the plurality of images, where $\alpha$ is an angular spacing between a subset of the images that belongs to a same bin, and T is a period of a physiological motion.

Other and further aspects and features will be evident from reading the following detailed description of the embodiments.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DESCRIPTION OF THE EMBODIMENTS

Figure 1A:
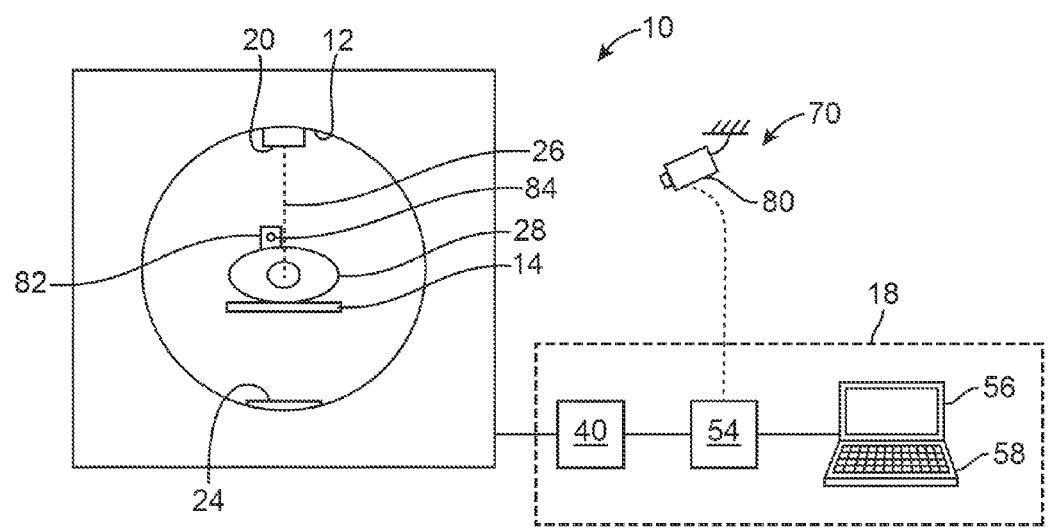
FIG. 1A illustrates a radiation system in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

Figure 1B:
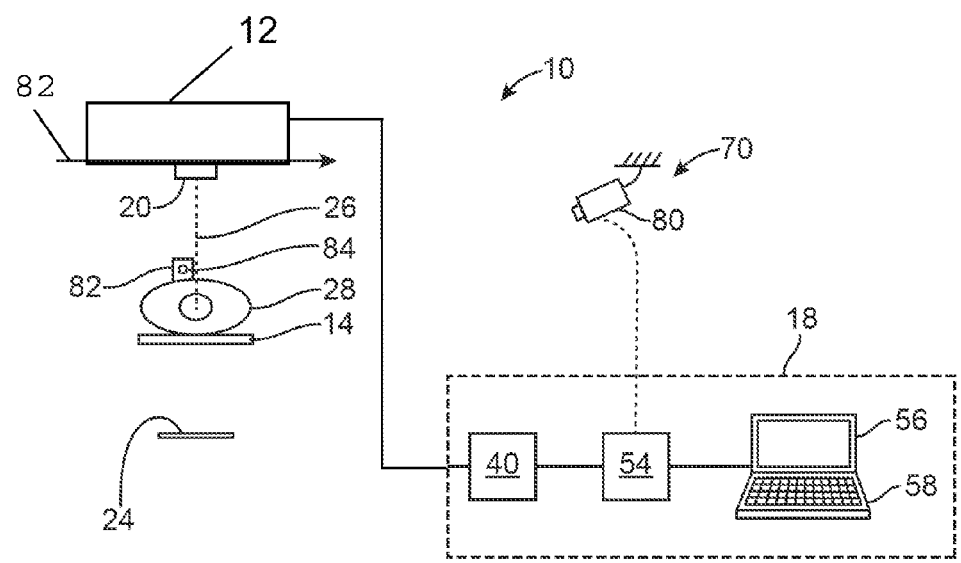
FIG. 1B illustrates another radiation system in accordance with other embodiments.

FIG. 1A illustrates a computed tomography system 10 in accordance with some embodiments. The system 10 includes a gantry 12, and a panel 14 for supporting a patient 28. The gantry 12 includes a radiation source 20 that projects a beam 26 of radiation (e.g., x-rays) towards a detector 24 on an opposite side of the gantry 12 while the patient 28 is positioned at least partially between the radiation source 20 and the detector (imager) 24. By means of non-limiting examples, the beam of x-rays can be a cone beam or a fan beam. The detector 24 has a plurality of sensor elements configured for sensing a x-ray that passes through the patient 28. Each sensor element generates an electrical signal representative of an intensity of the x-ray beam as it passes through the patient 28. The system 10 also includes a positioner (not shown) configured to move the radiation source 20. In some embodiments, the positioner may be configured to rotate the gantry 12 to thereby turn the radiation source 20 along a circular or an arc path. In some embodiments, the arc path may be curvilinear. In other embodiments, the arc path may be rectilinear (see FIG. 1B), which corresponds to an arc having an infinite radius.

The system 10 also includes a control system 18. In the illustrated embodiments, the control system 18 includes a processor 54, such as a computer processor, coupled to a control 40. The control system 18 may also include a monitor 56 for displaying data and an input device 58, such as a keyboard or a mouse, for inputting data. The operation of the radiation source 20 and the gantry 12 are controlled by the control 40, which provides power and timing signals to the radiation source 20, and controls a rotational speed and position of the gantry 12, based on signals received from the processor 54. Although the control 40 is shown as a separate component from the gantry 12 and the processor 54, in alternative embodiments, the control 40 can be a part of the gantry 12 or the processor 54.

In the illustrated embodiments, the radiation source 20 is a diagnostic radiation source for providing diagnostic energy. In other embodiments, in addition to, or instead of, being a diagnostic radiation source, the radiation source 20 may be a treatment radiation source for providing treatment energy. In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. In further embodiments, the radiation source 20 may be a treatment radiation source, in which cases, the imager 24 may be an on-board imager.

It should be noted that the system 10 is not limited to the configuration described above, and that the system 10 may have other configurations in other embodiments. For example, in other embodiments, the system 10 may have a different shape. In other embodiments, the radiation source 20 of the system 10 may have different ranges of motions and/or degrees of freedom. For example, in other embodiments, the radiation source 20 may be rotatable about the patient 28 completely through a 360° range, or partially through a range that is less than 360°. Also, in other embodiments, the radiation source 20 is translatable relative to the patient 28. Further, the radiation source 20 is not limited to delivering diagnostic energy in the form of x-ray, and may deliver treatment energy for treating a patient.

During a scan to acquire x-ray image data (projection data), the gantry 12 rotates about the patient 28 at different gantry angles, so that the radiation source 20 and the imager 24 may be used to obtain images at different gantry angles. As the system 10 is operated to obtain images at different gantry angles, the patient 28 is breathing. Thus, the resulting images at different gantry angles may correspond to different phases of a breathing cycle for the patient 28. After the scan is completed, or while the scan is continued to obtain additional projection images, the generated projection images at different gantry angles are stored, e.g., in a memory, and the projection images are processed to sort the images so that images that correspond to a same phase or a same phase range of a breathing cycle are binned (e.g., associated with each other). The binned images for a specific phase of a respiratory cycle can then be used to reconstruct a digital tomosynthesis image for that phase.

As shown in the figure, the system 10 may optionally further include a patient position determining system 70 that includes a camera 80 and a marker block 82 having a plurality of markers 84. The patient position determining system 70 is configured to determine amplitude and/or phase of a physiological movement of the patient 28. During use, the marker block 82 may be placed on the patient's chest, and the camera 80 is then used to view the markers 84 on the marker block 82. During a respiratory cycle, the chest of the patient 28 will move up and down, and the marker block 82 will move correspondingly. Because the relative positions among the markers 84 on the block 82 are known and pre-determined, by using this information, the processor 54 may be configured to process the image(s) from the camera 80 to determine a position of the marker block 82 relative to some arbitrary reference coordinate. By continuously tracking the position of the marker block 82, the processor 54 may determine the breathing amplitudes and/or phases of the breathing cycle that the patient 28 is going through. The determined amplitudes and/or phases may then be later used by the processor 54 to sort the images so that different sets of images correspond with respective phases or phase ranges of the breathing cycle, as similarly discussed.

Alternatively, the camera 80 may be configured to use other things as marker(s), such as a patient's clothes, a physiological feature of the patient 28, etc. Thus, in other embodiments, the marker block 82 may be optional, and the patient position determining system 70 may not include any marker block 82. In other embodiments, the patient position determining system 70 may be other systems known in the art, such as a strain-gauge for measuring chest expansion, etc., as long as the system can determine a state of the patient's 28 motion (e.g., breathing). Also, in further embodiments, signal emitting device(s), such as RF devices, may be coupled to a patient (e.g., implanted, or coupled to a patient's surface) for allowing breathing and other types of motion to be sensed.

Figure 2:
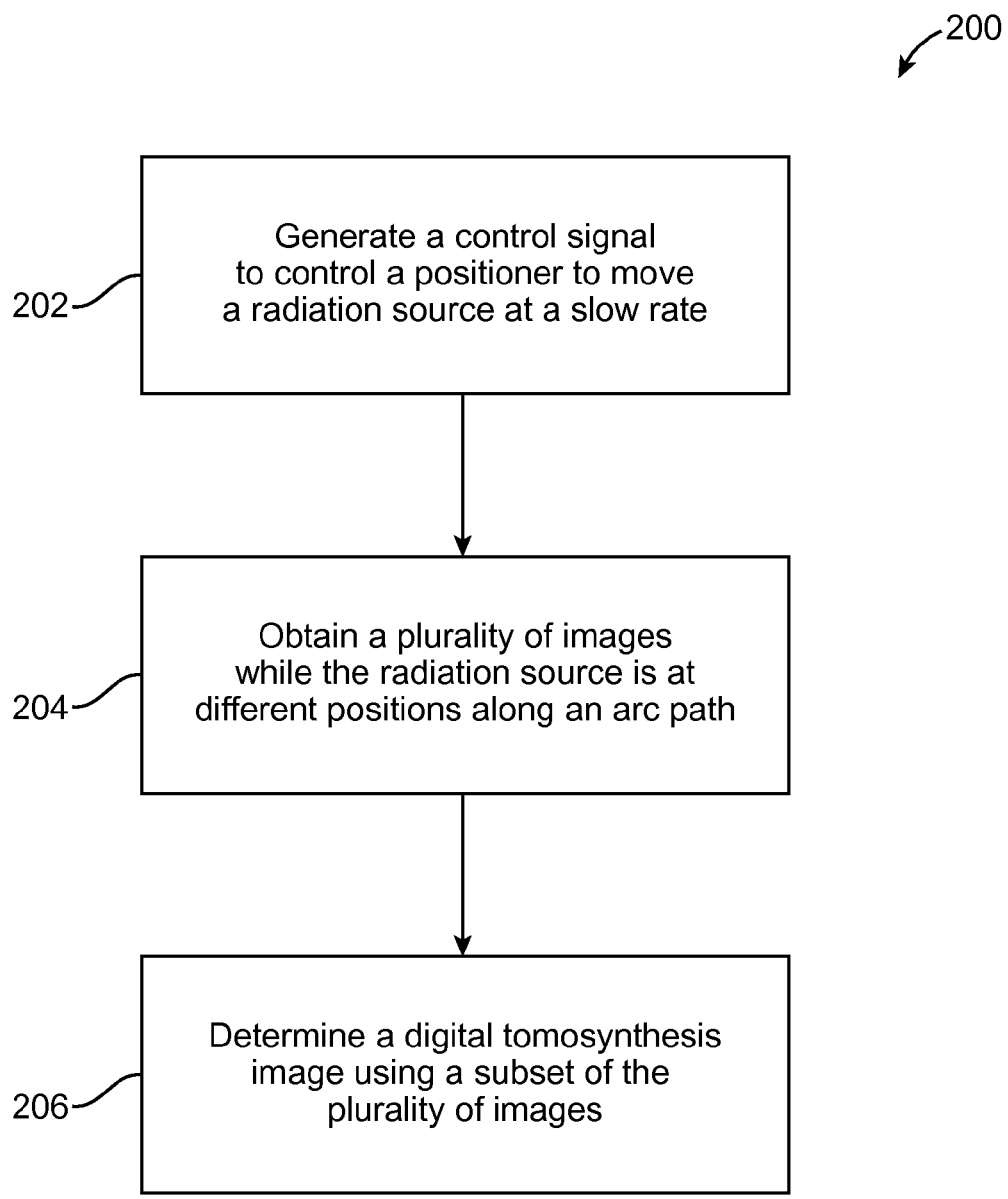
FIGS. 2-3 illustrate a method of obtaining tomosynthesis images in accordance with some embodiments.
Figure 3:
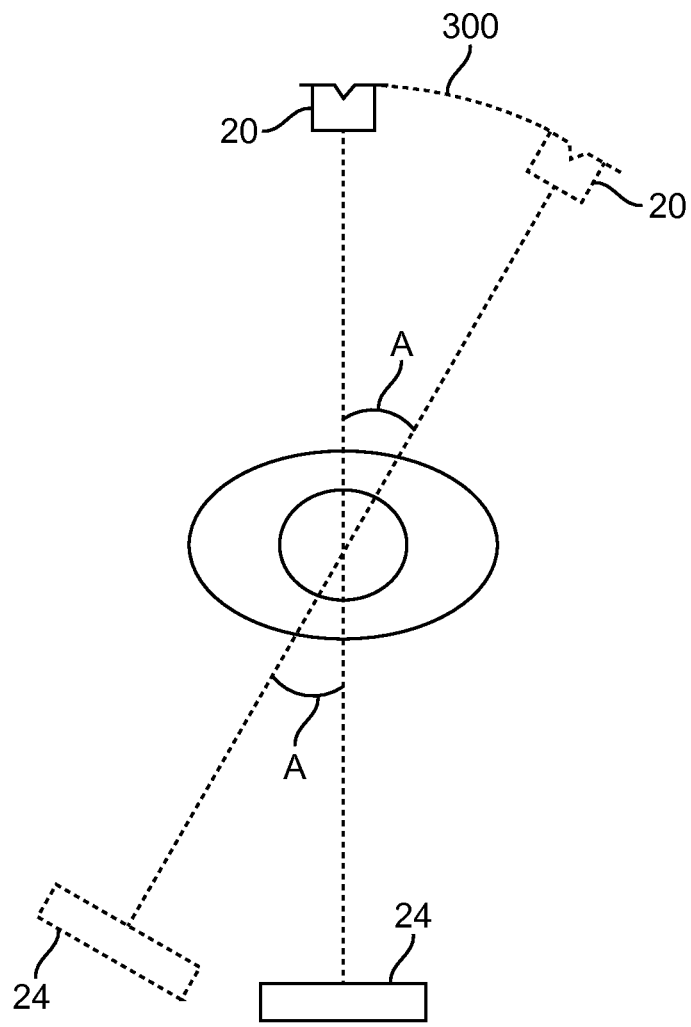

FIGS. 2 and 3 illustrate an imaging method 200 in accordance with some embodiments. The method 200 will be described with reference to the system 10 of FIG. 1A. However, it should be understood that the method 200 may be performed using other systems in other embodiments.

Before the method 200 is performed, the patient 28 is first positioned in an operative position so that the patient 28 is between the radiation source 20 and the imager 24. This may be accomplished during an imaging session, before a treatment session, during a treatment session, or after a treatment session. To perform the method 200, first, a control signal is generated to control the positioner to rotate the radiation source 20 through an angular range A (along an arc path 300) at a slow rate (Item 202) (FIG. 3).

In some embodiments, the rate at which the radiation source 20 is rotated may be based on a period T of physiological motion by the patient 28.

For example, in some embodiments, the processor 54 may receive the period T (which may be inputted by a user using the input device 58), and may then determine a desired rate of rotation by the radiation source 20 as a function of the period T. In some embodiments, the rate may be determined according to an equation $R_{max}=\alpha/T$, where $R_{max}$ is the maximum rate of rotation by the radiation source 20, and $\alpha$ is a desired angular spacing between the images to be acquired (i.e., the angular spacing between the images that will be used to construct a tomosynthesis image for a given phase or phase range). In some cases, the radiation source 20 may be configured to rotate at a rate R, which may be equal to the calculated rate $R_{max}$, or slower (i.e., $R<R_{max}$).

In some embodiments, the desired angular spacing a between the images may be 1 degree, which may be sufficient for avoiding aliasing effects in a tomosynthesis reconstruction for the purpose of removal of overlaying structures, such as bony anatomy, so that soft tissue may be visualized. In other embodiments, the desired angular spacing a between the images may be higher than 1 degree or less than 1 degree.

Also, for breathing motion, the period T may be any value from 3 seconds to 15 seconds (e.g., 4 seconds). For heart motion, the period T may be any value from 0.3 second to 1.5 seconds (e.g., 0.8 seconds). The processor may be configured to determine the rate of rotation based on the period T (whatever that value may be). In some embodiments, the period T may be entered by the user of the system 10 using the input device 58. In other embodiments, the period T may be determined by the processor 54 based on input from the patient position monitoring system 70 (e.g., a breathing monitor, a heart monitor, etc.). For example, in some embodiments, the processor 54 may be configured to calculate the period T of respiratory motion based on the image signals received from the camera 80 (or based on a signal representative of a state of a patient movement from another device).

After the processor 54 determines the rate R of rotation, the processor 54 may then generate a control signal to control the positioner in the system 10 to move the radiation source 20 at the determined rate R.

In other embodiments, the rate R at which the radiation source 20 rotates may be prescribed by a user. For example, in some embodiments, the user of the system 10 may configure the system 10 by entering the desired rate R into the processor 54 using the input device 58.

In the illustrated embodiments, the radiation source 20 is described as being rotated at a slow rate through along an arc path 300. For example, in some embodiments in which respiration motion is considered in an imaging process, the radiation source 20 may be rotated at a rate (which may be input by the user, or calculated by the processor 54 based on an input by the user) that is less than 0.6 degree/sec, and more preferably, less than 0.5 degree/sec, (e.g., 0.3 degree/sec or less, such as 0.125 degree/sec, etc.). These rates of rotation are considered examples of a "slow rate". In other embodiments, the slow rate of rotation may be faster than 0.6 degree/sec, but still slower than a rate of rotation in an existing tomosynthesis imaging system.

In other embodiments in which cardiac motion is considered in an imaging process, the radiation source 20 may be rotated at a rate (which may be input by the user, or calculated by the processor 54 based on an input by the user) that is less than 3.3 degree/sec, and more preferably, less than 2.5 degree/sec (e.g., 2 degree/sec or less, such as 1.25 degree/sec, 0.9 degree/sec, etc.). These rates of rotation are considered examples of a "slow rate". In other embodiments, the slow rate of rotation may be faster than 3.3 degree/sec, but still slower than a rate of rotation in an existing tomosynthesis imaging system.

In further embodiments, the rate may be considered slow if it is equal to, or less than, $\alpha/T$.

In the illustrated embodiments, the imager 24 may be coupled to the same gantry 12 to which the radiation source 20 is coupled. Thus, rotation of the gantry 12 to turn the radiation source 20 will cause a corresponding rotation of the imager 24, so that the radiation source 20 and the imager 24 are maintained on different sides of the patient 28 as they are rotated around the patient 28 along the arc path 300. In some embodiments, the control signal to control the positioner may be generated using the processor 54. As used in this specification, the term "signal" may refer to one or more signals.

Returning to FIG. 2, with reference to item 204, the processor 54 obtains a plurality of images that are generated using radiation 26 from the radiation source 20 while the radiation source 20 is at different positions along the arc path 300. In some embodiments, the arc path 300 has a corresponding arc angle A (angular range), and the angle A may be anywhere from 2 degrees to 10 degrees. In other embodiments, the arc angle A may be more than 10 degrees. In the illustrated embodiments, while the radiation source 20 is at different positions along the arc path 300, the radiation source 20 is activated to emit radiation towards the patient 28, and the imager 24 receives the radiation exiting from the patient 28. The imager 24 then generates images (projection images) in response to the received radiation, and passes the images to the processor 54. Thus, in some embodiments, the act of obtaining the images in item 204 of method 200 may be performed by the processor 54 receiving the images. In other embodiments, the act of obtaining the images may be performed by the imager 24, which generates the image signals for the images.

Figure 4A:
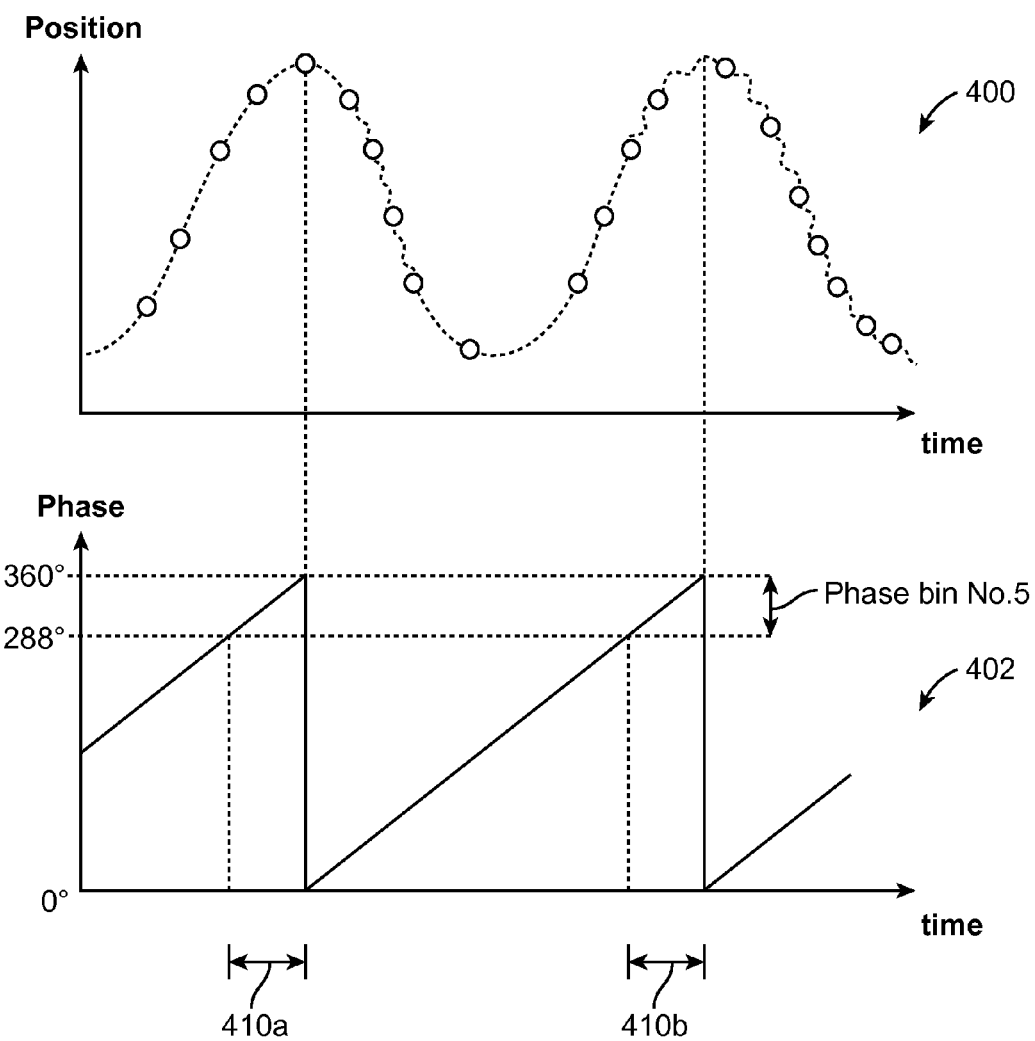
FIG. 4A illustrates a phase diagram aligned with a corresponding amplitude diagram in accordance with some embodiments.

Also, in the illustrated embodiments, while the imager 24 generates the images, the patient position monitoring system 70 is used to obtain position signals (e.g., in a form of camera images). The camera images are processed by the processor 54, which determines breathing amplitudes. FIG. 4A illustrates an example of the determined breathing amplitudes of respiratory cycles plotted against time to form an amplitude curve 400. In some embodiments, the processor 54 may also use the determined breathing amplitudes to determine phases of a respiratory cycle. A phase of a respiratory cycle represents a degree of completeness of the respiratory cycle. FIG. 4A also illustrates a phase curve 402 having phase values plotted against time, wherein the phase curve 402 corresponds with the amplitude curve 400. In the illustrated example, a phase value of 0° (and 360°) represents a peak of an inhale state, and the phase value varies linearly between 0° and 360° in a physiological cycle.

In the illustrated embodiments, for each image that is obtained while the patient is at a certain phase of a respiratory cycle, the processor 54 associate the image with the corresponding phase. The images and their respective associated phases may be stored in a non-transitory medium for later processing. Also, in some embodiments, the processor 54 may be configured to group (bin) images with different phase values together. For example, a user may prescribe a certain number of phase bins (e.g., 5 phase bins) using the input device 58. In such example, phase bins Nos. 1-5 will have respective phase ranges of 0°-72°, 72°-144°, 144°-216°, 216°-288°, and 288°-360°. One of the phase bins (phase bin No. 5) is illustrated in FIG. 4A. In such example, all images with phase values from 0°-72°, 72°-144°, 144°-216°, 216°-288°, and 288°-360° will be grouped by the processor 54 into phase bins Nos. 1-5, respectively. For example, with respect to phase bin No. 5, the processor 54 will bin the images that are generated during time periods 410a and 410b together into phase bin No. 5. Note that the duration of the time periods 410a, 410b in the example are not necessarily equal, and that they may be different, depending on the breathing pattern of the patient 28. In other embodiments, the prescribed number $N_B$ of phase bins may be more than 5 (e.g., 15 or more), or less than 5.

In some embodiments, in the case of respiratory motion, while the radiation source 20 is in different positions within the arc path 300, the images are generated at a frame rate FR that is at least 2 fps, and more preferably at least 3 fps (e.g., 3.75 fps). In other embodiments, in the case of heart motion, the images may be generated at a frame rate FR that is at least 10 fps, and more preferably at least 15 fps (e.g., 18.75 fps). In further embodiments, the frame rate FR may be different from the examples described. Also, in some embodiments, the frame rate FR may be calculated by the processor 54 based on an input from the user (e.g., using the input device 58). For example, in some embodiments, the user of the system 10 may enter a desired number $N_B$ of phase bins to the processor 54 (e.g., using the input device 58). The phase bin number $N_B$ prescribes how many segments (phase ranges) into which a physiological cycle is to be divided. After the phase bin number $N_B$ has been obtained (e.g., obtained by the processor 54 in response to an input transmitted by a user that prescribes the phase bin number), the processor 54 may then calculate the frame rate FR based on the equation $FR=N_B/T$, where T is a period of physiological cycle (e.g., breathing cycle, cardiac cycle, etc.). The calculated frame rate according to this equation may be used as the minimum required frame rate. In other embodiments, the frame rate FR may be prescribed by the user. For example, in some embodiments, the user of the system 10 may configure the system 10 by entering the desired frame rate FR into the processor 54 using the input device 58.

Also, in some embodiments, while the radiation source 20 is at different positions along the arc path 300, at least 60 images (e.g., 90 images) are generated using the radiation source 20 and the imager 24. In other embodiments, there may be more than 90 images or fewer than 90 images generated while the radiation source 20 is at different position along the arc path 300. In some embodiments, the number of images N generated when the radiation source 20 is at different positions along the arc path 300 may be a function of A, $N_B$, and $\alpha$, where A is the arc angle of the arc path 300, and $N_B$ is a prescribed number of phase bins. For example, the number of images N may be based on the equation $N=A*N_B/\alpha$. In other embodiments, the number of images N generated may be a function of A, FR, T, and $\alpha$, where FR is the frame rate for the imager 24. For example, the number of images N may be based on the equation $N=A*FR/(T*\alpha)$. In some embodiments, any one or combination of the parameters A, $N_B$, FR, T, and $\alpha$ may be selectively prescribed by a user of the system 10 using the input device 58. In other embodiments, any one or combination of the parameters A, $N_B$, FR, T, and $\alpha$ may be pre-set in the system 10.

Returning to FIG. 2, after the processor 54 has obtained the images, the processor 54 then determines a digital tomosynthesis image using a subset of the plurality of images obtained within the arc length (item 206). In the illustrated embodiments, the processor 54 is configured to select the subset of images that belong to a same phase bin (prescribed phase range), and use the selected subset of images to construct the digital tomosynthesis image. The act 206 may be repeated for other subsets of images for other respective phase bins (phase ranges) to obtain additional tomosynthesis image(s). In some embodiments, the processor 54 may be configured to reconstruct the digital tomosynthesis image(s) using the projection images based on an algorithm that is similar to that for CT image reconstruction. However, unlike a CT image, each tomosynthesis image is constructed using a set of projection images that are less than those for a CT image.

Figure 4B:
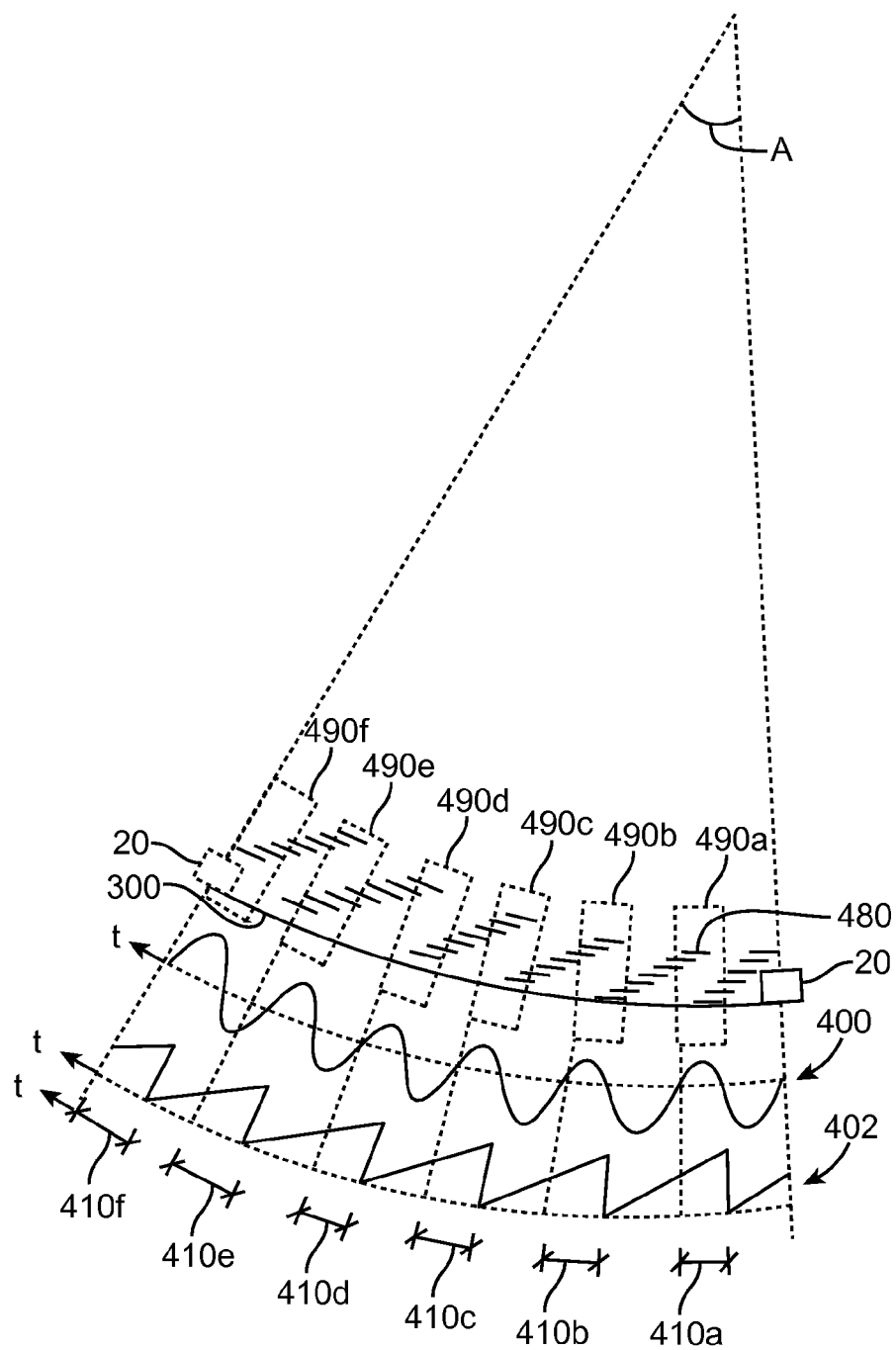
FIG. 4B illustrates rotation of a radiation source along an arc path with an arc angle.

To graphically illustrate items 202-206 of method 200, refer to FIG. 4B, which illustrates rotating the radiation source 20 along the arc path 300 with arc angle A. While the radiation source 20 is at different positions along the arc path 300, it cooperates with the imager 24 to generate images 480. Each of the lines 480 in the figure represents an image obtained at an instance in time. In the illustrated example, the arc angle A may be 6°, the period T of respiration of the patient 28 may be 4 second, and the desired angular separation $\alpha$ between images in a same phase bin may be 1°. Thus, the rate R of rotation may be $\alpha/T=0.25°/sec$. Accordingly, to move the radiation source 20 at the rate R=0.25°/sec through the arc angle A=6° would require 24 seconds. During this period, there may be approximately 24/T=6 respiratory cycles, as graphically shown by the amplitude chart 400. It should be noted that the number (e.g., 6) of respiratory cycles in the example is an approximate number (e.g., 6±2) because breathing period may change. The corresponding phase diagram 402 is also shown. Thus, in the illustrated example, there is at least one respiratory cycle for each angular separation $\alpha=1°$. Assuming that the user has prescribed the number $N_B$ of phase bins to be 5, the images 480 generated would be grouped into five different phase bins based on the phases of the respiratory cycle at which the respective images are generated. As shown in the figure, the images 490a-490f (collectively being a subset of the images 480), which are generated respectively during the time periods 410a-410f, are binned into phase bin No. 5 because these images are generated when the respiratory phase of the patient 28 is anywhere between 288°-360° (like the example shown in FIG. 4A). Thus, when the processor 54 generates the tomosynthesis image for phase bin No. 5, the processor 54 uses the approximately 6 images 490a-490f from phase bin No. 5, and construct the tomosynthesis image using these images. The processor 54 may apply the same technique for generating additional tomosynthesis images for the other phase bins (Nos. 1-4).

Also, let us assume that the frame rate FR is selected to be at least $N_B/T=5/4$ sec=1.25 frames per second (fps). In such cases, there will be at least 5 image frames (=1.25 frames/sec*4 sec/cycle) for each respiratory cycle, or at least 1 image frame (=5 image frames/5 phase bins) in each of the image groups 490a-490f for a given phase bin (phase bin No. 5 in the example). In this example, when the processor 54 generates the tomosynthesis image for phase bin No. 5, it will have 6 groups 490a-490f of 1 image=6 images available in the bin, with each of the groups 490a-490f separated by an angular spacing that is $\alpha=1°$ for that phase bin (bin No. 5).

It should be noted that in some embodiments, the frame rate and rotation rate are fixed, and the angular spacing a (e.g., 1 degree spacing) is prescribed (therefore guaranteed) to avoid wagon wheel effect. Also, because the patient breathing period may vary, the number of projections available in each phase bin for tomosynthesis may not be 6 in the example, and may be approximately 6 (e.g., 6±2). Also, in other embodiments, instead of setting the frame rate FR to be the minimum ($N_B/T$), the frame rate FR may be set higher than this minimum.

As illustrated in the above example, the system 10 and the method 200 are advantageous because the projection images in each phase bin for constructing a tomosynthesis image may be set to have a uniform angular spacing (e.g., due to an input that led to selecting R=1 degree/T). As a result the obtained projection images may have a substantially uniform angular spacing (e.g., angular spacing between adjacent images that do not vary by more than 20%, such as 0%). As illustrated in the above example, the images for constructing a tomosynthesis image for a given phase bin have an angular spacing that is $\alpha$ (=1° in the above example). Also, because the tomosynthesis image technique requires less projection images (compared to CBCT), the radiation dose to the patient 28 is reduced compared to that of 4D CBCT. In some embodiments, the field of view by the radiation source 20 may be collimated (using a collimator) to only the volume of interest, thereby further reducing the imaging dose.

In some embodiments, after the tomosynthesis images have been constructed, the tomosynthesis images may be stored in a non-transitory medium for later use (e.g., processing). Alternatively, or additionally, after the tomosynthesis images have been constructed, the processor 54 may transmits the images to a screen for display. Also, in some embodiments, the screen may display a part of the digital tomosynthesis image over one of the projection images. In such cases, the part of the tomosynthesis image is aligned with the projection image so that the same tissue structures in both images are aligned. In one implementation, the tomosynthesis image may be combined with the projection image as an inset. The inset display may be turned on and off at a comfortable frequency so that in the inset area of the display, the presentation alternates between the tomosynthesis image and the input projection image. In another implementation, color wash may be used to display the digital tomosynthesis image as an overlay to the gray background projection.

Also, in some embodiments, the tomosynthesis images for the different respective phase bins may be stored in a format that allows them to be displayed in a sequence in a form of a video. In further embodiments, if the tomosynthesis images are combined with the respective projection images, the combined images may be viewed as a video when displayed sequentially. In order to maintain proper temporal alignment between the digital tomosynthesis image and the projection image (background image), the tomosynthesis image is chosen (from the set of tomosynthesis images at different respective phase bins) so that the phase value associated with the tomosynthesis image is closest to that of the projection image being displayed.

In the above embodiments, the method 200 has been described as a "one-shot" process in which a sequence of tomosynthesis images is generated, and the sequence is then displayed in the screen. In other embodiments, the source rotation and image acquisition may be a continuous process. In such continuous process, the latest projection images acquired over a specified arc length may be used for the digital tomosynthesis image reconstruction. In some embodiments, FIFO acquisition scheme may be employed, in which for every new acquired projection image, the oldest projection image is discarded, and the digital tomosynthesis image is constructed using the updated set of projection images. Thus, each tomosynthesis image for a given phase may be continuously updated, using some of the previously acquired projection images (for the same phase), and the newly acquired projection image (for the same phase). This results in the sequence of the tomosynthesis images at different phases being displayed in a video format, with each of the tomosynthesis images in the video being updated based on the latest projection image(s). Also, in other embodiments, the video that is continuously updated may be the current input projection image with the latest tomosynthesis image as an inset or overlay. The inset or overlay image is selected from the available phase bins such that its phase is closest to the phase of the current projection being displayed, namely the current breathing phase of the patient as measured by the breathing sensor, e.g. the camera system.

Also, in the above embodiments, the system 10 and the method 200 have been described as rotating the radiation source 20 in one direction. In other embodiments, the radiation source 20 may be configured to rotate in a back-and-forth motion. Such configuration may be employed to implement the image acquisition in a continuous process, as discussed.

Also, in one or more embodiments, the system 10 may include a moving radiation source 20 (e.g., a rotatable or translatable radiation source 20) while the imager 24 remains in a fixed position. Such system 10 may allow tomosynthesis images to be obtained using the embodiments of the techniques described herein.

Figure 5:
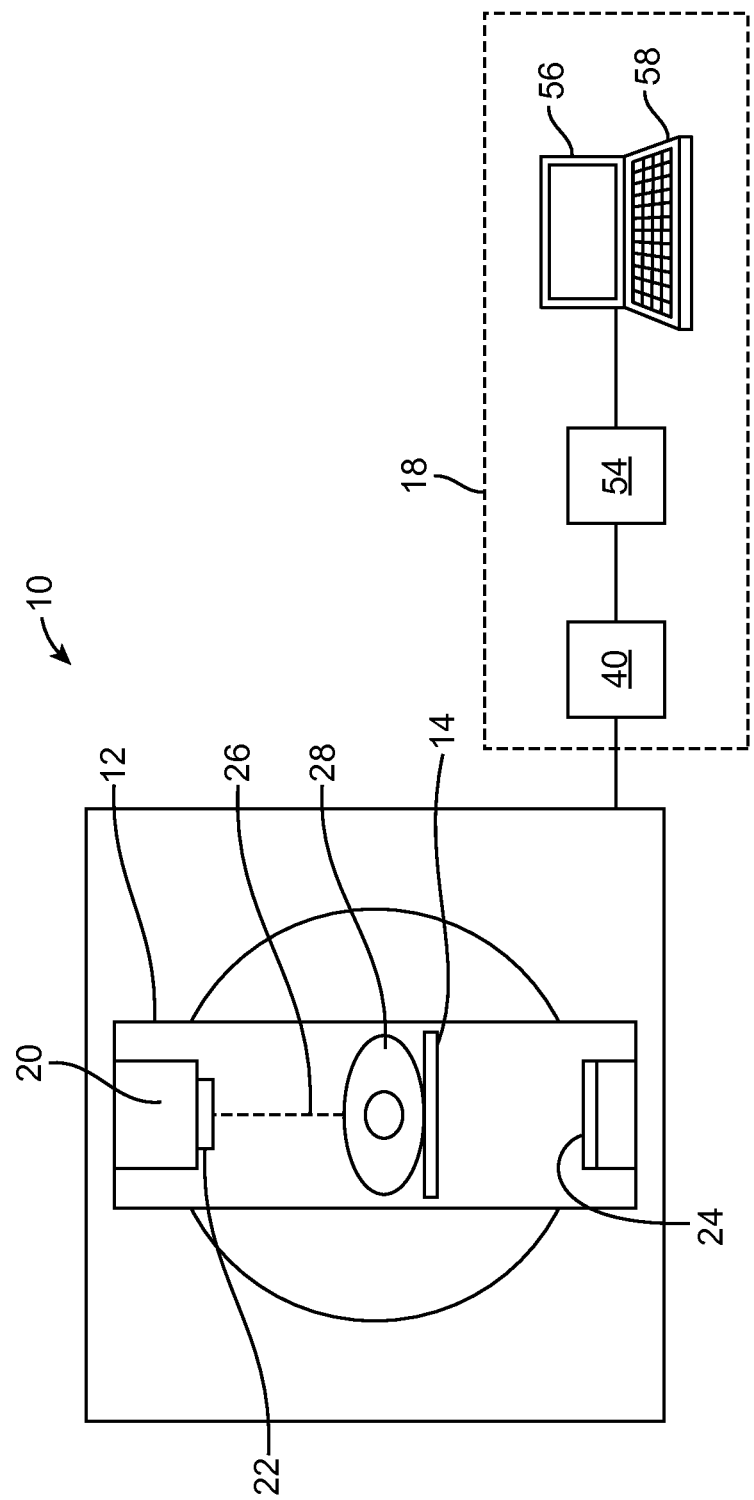
FIG. 5 illustrates another radiation system in accordance with other embodiments.

It should be noted that the system 10 that may be used to generate image(s) for use in the method 200 is not limited to the example described previously. For example, in other embodiments, other imaging systems having different configurations may be used. For example, FIG. 5 illustrates another embodiment of the system 10 that may be used. The system 10 of FIG. 5 is a radiation system that includes a gantry 12, a patient support 14 for supporting a patient, and a control system 18 for controlling an operation of the gantry 12. The gantry 12 is in a form of an arm. The system 10 also includes a radiation source 20 that projects a beam 26 of radiation towards a patient 28 while the patient 28 is supported on support 14, and optionally a collimator system 22 for controlling a delivery of the radiation beam 26. The radiation source 20 can be configured to generate a cone beam, a fan beam, or other types of radiation beams in different embodiments. In the illustrated embodiments, the radiation source 20 is a diagnostic radiation source for providing diagnostic energy. In other embodiments, in addition to, or instead of, being a diagnostic radiation source, the radiation source 20 may be a treatment radiation source for providing treatment energy.

Figure 6A:
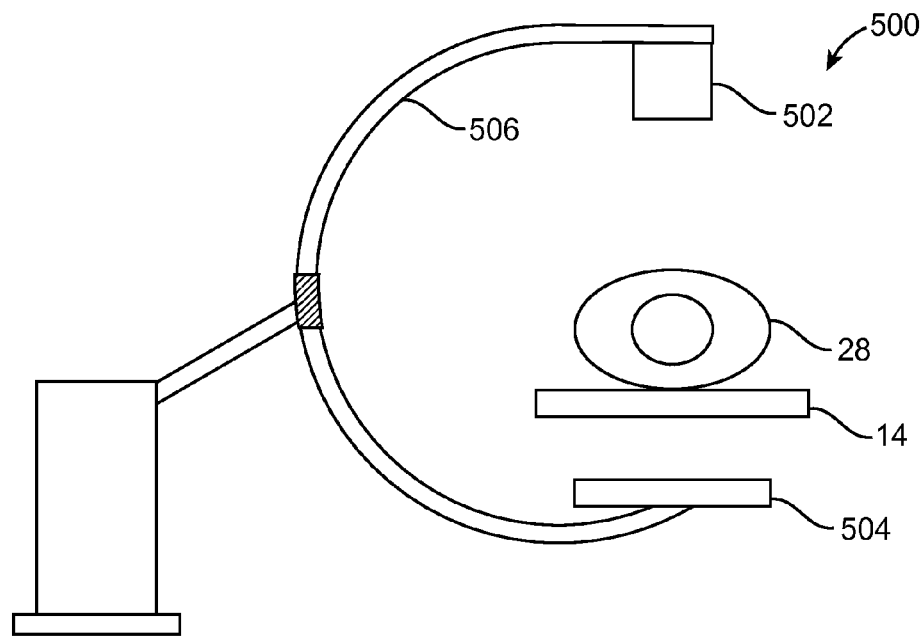
FIG. 6A illustrates another radiation system in accordance with other embodiments.
Figure 6B:
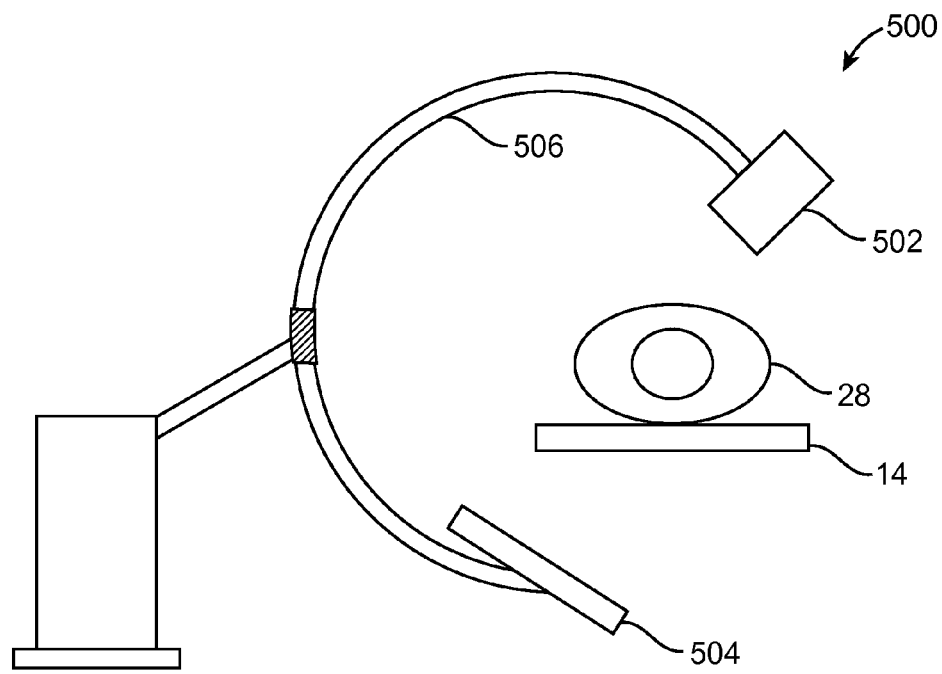
FIG. 6B illustrates the radiation system of FIG. 6A, showing the source has been rotated.

FIGS. 6A and 6B illustrate another system 500 that may be used to provide image(s) for use in the method 200 in accordance with some embodiments. The system 500 is a fluoroscopic system, and includes an x-ray source 502, an imager 504, and an arm (e.g., C-arm) 506 coupled to the source 502 and the imager 504. When using the fluoroscopic system 500 to perform the method 200, the x-ray source 502 and the imager 504 may be placed at a first position (FIG. 6A). The x-ray source 502 and the imager 504 may then be rotated along an arc path to a second position (FIG. 6B). While the x-ray source 502 is at different positions along the arc path, the x-ray source 502 delivers x-ray beams to generate a first sequence of images using the imager 504 while the patient 28 is undergoing respiratory motion (like that described with reference to item 204 in the method 200). A processor of the system 500 then sorts the images obtained in the arc path so that different images that correspond with a certain phase range are grouped (binned) together. The processor of the system 500 then constructs different tomosynthesis images using the respective grouped images. The tomosynthesis images can then be displayed in their phase order so that they form a video.

In other embodiments, the system 10 may be considered to be a part of a treatment radiation system, or may be integrated with a treatment radiation system. For example, in some embodiments, the radiation source 20 and the imager 24 of the system 10 may be placed next to a treatment radiation system, so that the imaging method 200 of FIG. 2 may be performed before, during, and/or after a treatment session performed using the treatment radiation system. In some embodiments, the radiation source 20 and the imager 24 of the system 10 may be coupled to a gantry that is separate from that for the treatment radiation system. In other embodiments, the radiation source 20 and/or the imager 24 of the system 10 may be coupled to a room (e.g., room-based). For example, in some embodiments, the imager 24 may be fixedly or moveably coupled to a floor in a room while the movable source is attached to the ceiling. In other embodiments, the radiation source 20 and the imager 24 of the system 10 may be coupled to a same gantry as that for the treatment radiation system. For example, in other embodiments, the system 10 of FIG. 1A may further include a treatment radiation source coupled to the gantry 12. The treatment radiation source may be oriented relative to the diagnostic radiation source 20 at 90° or at any of other angles. In such system, the imaging method 200 may be performed using the diagnostic radiation source 20 and the imager 24 before, during, and/or after a treatment session performed using the treatment radiation system.

In further embodiments, the rotation of the radiation source 20 and the imager 24 may be in a plane that forms an angle with a plane of rotation by the treatment radiation source.

Also, in other embodiments, instead of having one radiation source 20 and one imager 24, the system 10 may include two or more radiation sources 20, and two or more corresponding imagers 24. The system 10 may be a diagnostic system that is separate from a treatment radiation system, or may be integrated with the treatment radiation system (e.g., they may share a common gantry). Also, in some embodiments, the multiple radiation sources 20 and/or the multiple imagers 24 may be coupled to a room (e.g., room-based). For example, in some embodiments, the imagers 24 may be fixedly or moveably coupled to a floor in a room while its corresponding source is attached to the ceiling. In some embodiments, the system 10 may have two radiation sources 20 that are coupled to the same gantry 12, and are oriented 90° relative to each other. The system 10 may also have two corresponding imagers 24 that are oriented 90° relative to each other. Alternatively, the first pair of radiation source 20 and imager 24 may be coupled to a first gantry 12, and the second pair of radiation source 20 and imager 24 may be coupled to a second gantry 12 that is next to the first gantry in a side-by-side configuration. In either system, the method 200 of FIG. 2 may be performed two times using the respective first and second radiation sources 20, and the respective first and second imagers 24. For example, during use, the two radiation sources 20 and the two imagers 24 may be rotated simultaneously along respective arc paths. While the first radiation source 20 is at different positions along its arc path, it delivers radiation towards the patient 28, and the corresponding imager 24 then generates images in response to the detected radiation exiting the patient 28. Similarly, while the second radiation source 20 is at different positions along its arc path, it delivers radiation towards the patient 28, and the corresponding imager 24 then generates images in response to the detected radiation exiting the patient 28. As a result, two sets of projection images are obtained for the respective two different arc paths. In some embodiments, the two radiation sources may activate simultaneously to create the two sets of images. For each set of projection images, the processor 54 may then determine a sequence of tomosynthesis images, as similarly discussed.

Figure 7:
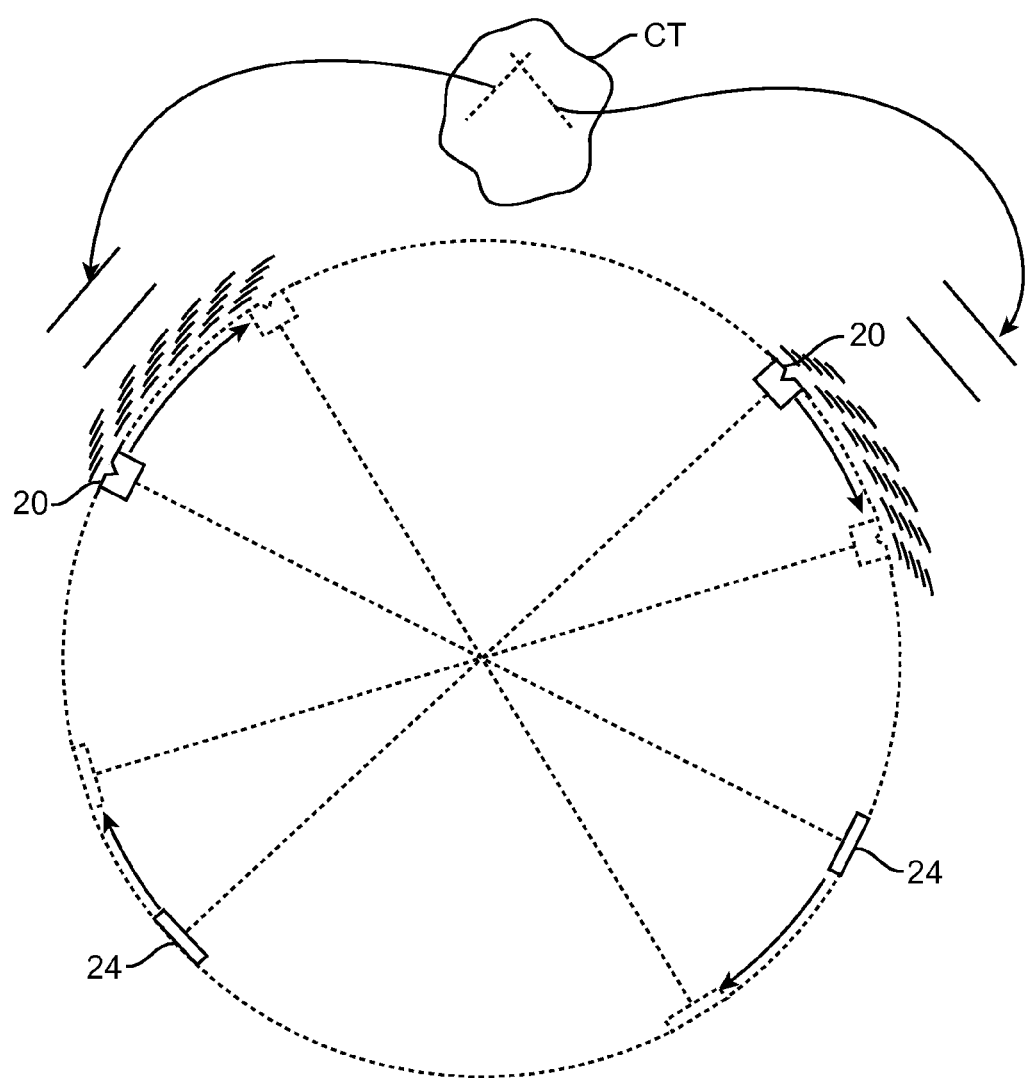
FIG. 7 illustrates two sets of projection images in accordance with some embodiments.

In some embodiments, the two sets of projection images (such as those shown in FIG. 7) obtained for the two different respective arc paths may be used to track a position of a target in a three dimensional space. In particular, the tumor position in the resulting DTS images may be tracked with a corresponding suitable reference template, for example constructed for each arc acquisition from the plan CT. In some embodiments, the processor may be configured to obtain the reference template by determining a portion of a volumetric image that corresponds with a plane of a tomosynthesis image, and compare the portion of the volumetric image with the tomosynthesis image. Using the sequential stereo (or conventional stereo in the case of room-based system) the two sequences of pixel-domain track points are combined to estimate the 3D trajectory of the markerless target as a function of respiration phase. For example, in one implementation, a reference CT image (e.g., from planning) may be available. By forward projection and digitally simulating the DTS image reconstruction, the processor may simulate DTS images of the target corresponding to the geometry of DTS image from each arc (e.g., two separate arcs on the same gantry, or the two arcs of a stereo imaging pair). These simulated images may be used as templates for template matching to each of the DTS image constructed from the treatment time projections. If successful, the match point of the template may be the track point in that DTS image. The DTS images as function of phase form a sequence. The sequence of track points found in each sequence (one sequence for each arc) are associated with each other thus forming stereo point pairs that may be used to triangulate to a point in 3D space.

It should be noted that as used in this specification, the term "processor" (such as the processor 54) may refer to one or more processing units, such as one or more processors, which may or may not be a part of the system 10. Also, one or more functions described with reference to the processor 54 may be performed at least in part by the processor 54, completely by the processor 54, or completely by another processor (which may or may not be a part of the system 10).

Also, the term "image" need not be limited to an image that is displayed visually, and may refer to image data that is stored. Also, the term "processor" may include one or more processing units, and may refer to any device that is capable of performing mathematical computation implemented using hardware and/or software. Further, in any of the embodiments described herein, instead of using the processor 54 to perform the various functions described, a separate processor may be used. In addition, it should be noted that the terms "first" and "second" (e.g., as in "first digital tomosynthesis image" and "second digital tomosynthesis image", etc.) refer to two things/items that are different or separate, and therefore, do not necessarily refer to the order in which the things are generated or arranged.

Computer System Architecture

Figure 8:
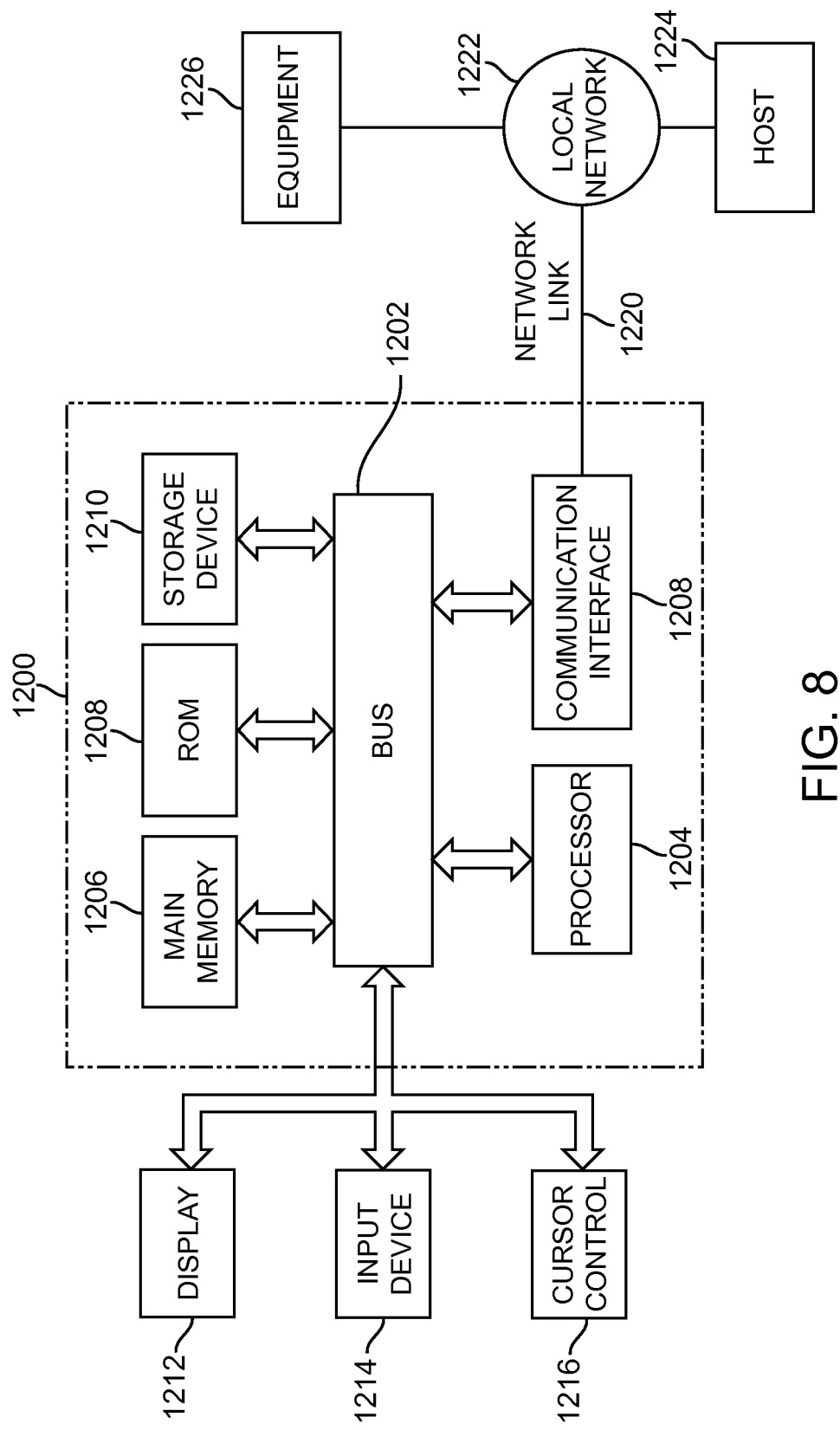
FIG. 8 is a block diagram of a computer system architecture, with which embodiments described herein may be implemented.

FIG. 8 is a block diagram that illustrates an embodiment of a computer system 1200 upon which an embodiment of the invention may be implemented. Computer system 1200 includes a bus 1202 or other communication mechanism for communicating information, and a processor 1204 coupled with the bus 1202 for processing information. The processor 1204 may be an example of the processor 54 of FIG. 1A/1B, or another processor that is used to perform various functions described herein. In some cases,the computer system 1200 may be used to implement the processor 54. The computer system 1200 also includes a main memory 1206, such as a random access memory (RAM) or other dynamic storage device, coupled to the bus 1202 for storing information and instructions to be executed by the processor 1204. The main memory 1206 also may be used for storing temporary variables or other intermediate information during execution of instructions to be executed by the processor 1204. The computer system 1200 further includes a read only memory (ROM) 1208 or other static storage device coupled to the bus 1202 for storing static information and instructions for the processor 1204. A data storage device 1210, such as a magnetic disk or optical disk, is provided and coupled to the bus 1202 for storing information and instructions.

The computer system 1200 may be coupled via the bus 1202 to a display 1212, such as a cathode ray tube (CRT), for displaying information to a user. An input device 1214, including alphanumeric and other keys, is coupled to the bus 1202 for communicating information and command selections to processor 1204. Another type of user input device is cursor control 1216, such as a mouse, a trackball, or cursor direction keys for communicating direction information and command selections to processor 1204 and for controlling cursor movement on display 1212. This input device typically has two degrees of freedom in two axes, a first axis (e.g., x) and a second axis (e.g., y), that allows the device to specify positions in a plane.

The computer system 1200 may be used for performing various functions (e.g., calculation) in accordance with the embodiments described herein. According to one embodiment, such use is provided by computer system 1200 in response to processor 1204 executing one or more sequences of one or more instructions contained in the main memory 1206. Such instructions may be read into the main memory 1206 from another computer-readable medium, such as storage device 1210. Execution of the sequences of instructions contained in the main memory 1206 causes the processor 1204 to perform the process steps described herein. One or more processors in a multi-processing arrangement may also be employed to execute the sequences of instructions contained in the main memory 1206. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 1204 for execution. Such a medium may take many forms, including but not limited to, non-volatile media, volatile media, and transmission media. Non-volatile media includes, for example, optical or magnetic disks, such as the storage device 1210. A non-volatile medium may be considered to be an example of a non-transitory medium. Volatile media includes dynamic memory, such as the main memory 1206. A volatile medium may be considered to be another example of a non-transitory medium. Transmission media includes coaxial cables, copper wire and fiber optics, including the wires that comprise the bus 1202. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1204 for execution. For example, the instructions may initially be carried on a magnetic disk of a remote computer. The remote computer can load the instructions into its dynamic memory and send the instructions over a telephone line using a modem. A modem local to the computer system 1200 can receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1206, from which the processor 1204 retrieves and executes the instructions. The instructions received by the main memory 1206 may optionally be stored on the storage device 1210 either before or after execution by the processor 1204.

The computer system 1200 also includes a communication interface 1218 coupled to the bus 1202. The communication interface 1218 provides a two-way data communication coupling to a network link 1220 that is connected to a local network 1222. For example, the communication interface 1218 may be an integrated services digital network (ISDN) card or a modem to provide a data communication connection to a corresponding type of telephone line. As another example, the communication interface 1218 may be a local area network (LAN) card to provide a data communication connection to a compatible LAN. Wireless links may also be implemented. In any such implementation, the communication interface 1218 sends and receives electrical, electromagnetic or optical signals that carry data streams representing various types of information.

The network link 1220 typically provides data communication through one or more networks to other devices. For example, the network link 1220 may provide a connection through local network 1222 to a host computer 1224 or to equipment 1226 such as a radiation beam source or a switch operatively coupled to a radiation beam source. The data streams transported over the network link 1220 can comprise electrical, electromagnetic or optical signals. The signals through the various networks and the signals on the network link 1220 and through the communication interface 1218, which carry data to and from the computer system 1200, are exemplary forms of carrier waves transporting the information. The computer system 1200 can send messages and receive data, including program code, through the network(s), the network link 1220, and the communication interface 1218.

Although particular embodiments have been shown and described, it will be understood that it is not intended to limit the claimed inventions, and it will be obvious to those skilled in the art that various changes and modifications may be made. The specification and drawings are, accordingly, to be regarded in an illustrative rather than restrictive sense. The claimed inventions are intended to cover alternatives, modifications, and equivalents.

What is claimed:

1. An imaging system, comprising:
    a radiation source;
    a positioner configured to rotate the radiation source along an arc path at a rate that is equal to or less than $R_{max}$, $R_{max}$ being calculated from $\alpha$ and T using a processing unit, and being equal to $\alpha/T$, wherein the rate is a speed of rotation of the radiation source when the radiation source is rotating;
    an imager in operative position relative to the radiation source, wherein the radiation source and the imager are configured to obtain a plurality of images while the radiation source is at different positions along the arc path; and
    a processor configured to determine a digital tomosynthesis image using a subset of the plurality of images;
    where $\alpha$ is an angular spacing between a subset of the images that belongs to a same bin, and T is a period of a physiological motion, wherein at least two images in the subset of the images belonging to the same bin correspond with two different respective positions of the radiation source.

2. The imaging system of claim 1, wherein the rate is less than $\alpha/T$, and the rate has a value that is a function of the period T of physiological motion.

3. The imaging system of claim 1, wherein the images are for a target undergoing respiratory motion, and the rate at which the positioner is configured to move the radiation source is less than 0.4 degree/sec.

4. The imaging system of claim 1, wherein the images are for a target undergoing respiratory motion, and the rate at which the positioner is configured to move the radiation source is less than 0.3 degree/sec.

5. The imaging system of claim 1, wherein the images are for a target undergoing cardiac motion, and the rate at which the positioner is configured to move the radiation source is less than 3.3 degree/sec.

6. The imaging system of claim 1, wherein the images are for a target undergoing cardiac motion, and the rate at which the positioner is configured to move the radiation source is less than 2 degree/sec.

7. The imaging system of claim 1, wherein the arc path has a corresponding arc angle that is anywhere from 2 degrees to 10 degrees.

8. The imaging system of claim 1, wherein the radiation source and the imager are configured to obtain the plurality of images at a frame rate that is equal to or higher than $N_B/T$, wherein $N_B$ is a prescribed number of bins.

9. The imaging system of claim 1, wherein the plurality of images comprises at least 60 images that are obtained while the radiation source is at the different positions along the arc path, and the arc path has a corresponding arc angle that is less than 10 degrees.

10. The imaging system of claim 1, wherein the radiation source and the imager are configured to obtain the plurality of images at a frame rate that is at least 2 fps.

11. The image system of claim 1, wherein the processor is configured to display at least a part of the digital tomosynthesis image over one of the plurality of images.

12. The image system of claim 1, wherein the radiation source and the imager are configured to obtain an additional plurality of images, and the processor is further configured to update the digital tomosynthesis image using the subset of the plurality of images and at least one of the additional plurality of images.

13. The image system of claim 1, wherein the plurality of images comprises different image sets, each of the image sets comprises images that correspond with a phase or a phase range of a physiological cycle, and wherein the processor is configured to determine the digital tomosynthesis image using one of the image sets.

14. The image system of claim 13, wherein the images in each of the image sets have a substantially uniform angular spacing.

15. The image system of claim 1, wherein the processor is further configured to obtain a portion of a volumetric image that corresponds with a plane of the tomosynthesis image, and compare the portion of the volumetric image with the tomosynthesis image.

16. The image system of claim 1, wherein the processor is further configured to:
    determine a first digital tomosynthesis image and a second digital tomosynthesis images using at least some of the plurality of images obtained while the radiation source is at the different positions along the arc path; and
    outputting the first and second digital tomosynthesis images for display on a screen in a form of a video.

17. The image system of claim 1, wherein the radiation source is coupled to a C-arm.

18. The image system of claim 1, wherein the imager is coupled to a floor.

19. The image system of claim 1, wherein the positioner is configured to rotate the radiation source in a single rotational direction.

20. The image system of claim 1, wherein the positioner is configured to rotate the radiation source in two opposite rotational directions.

21. The image system of claim 1, wherein the arc path is rectilinear with a corresponding infinite arc radius.

22. An imaging method, comprising:
    generating a control signal to control a positioner to rotate a radiation source through an arc path at a rate that is equal to or less than $R_{max}$, $R_{max}$ being calculated from $\alpha$ and T using a processing unit, and being equal to $\alpha/T$, wherein the rate is a speed of rotation of the radiation source when the radiation source is rotating; and
    obtaining a plurality of images that are generated using radiation from the radiation source while the radiation source is at different positions along the arc path; and
    determining a digital tomosynthesis image using a subset of the plurality of images;
    where $\alpha$ is an angular spacing between a subset of the images that belongs to a same bin, and T is a period of a physiological motion, wherein at least two images in the subset of the images belonging to the same bin correspond with two different respective positions of the radiation source.

23. The method of claim 22, further comprising obtaining:
the period T of physiological motion; and
determining the rate as a function of the period T.

24. The method of claim 22, wherein the images are for a target undergoing respiratory motion, and the rate is less than 0.4 degree/sec.

25. The method of claim 22, wherein the images are for a target undergoing respiratory motion, and the rate is less than 0.3 degree/sec.

26. The method of claim 22, wherein the images are for a target undergoing cardiac motion, and the rate is less than 3.3 degree/sec.

27. The method of claim 22, wherein the images are for a target undergoing cardiac motion, and the rate is less than 2 degree/sec.

28. The method of claim 22, wherein the arc path has an arc angle that is anywhere from 2 degrees to 10 degrees.

29. The method of claim 22, wherein the images are generated at a frame rate that is equal to or higher than $N_B/T$, wherein $N_B$ is a prescribed number of bins.

30. The method of claim 22, wherein the images comprises at least 60 images that are obtained while the radiation source is at the different positions along the arc path, and the arc path has a corresponding arc angle that is less than 10 degrees.

31. The method of claim 22, wherein the images are generated at a frame rate that is at least 2 fps.

32. The method of claim 22, further comprising displaying at least a part of the digital tomosynthesis image over one of the plurality of images.

33. The method of claim 22, further comprising obtaining an additional plurality of images, and updating the digital tomosynthesis image using the subset of the plurality of images and at least one of the additional plurality of images.

34. The method of claim 22, wherein the plurality of images comprises different image sets, each of the image sets comprises images that correspond with a phase or a phase range of a physiological cycle, and wherein the digital tomosynthesis image is generated using one of the image sets.

35. The method of claim 34, wherein the images in each of the image sets have a substantially uniform angular spacing.

36. The method of claim 22, further comprising:
obtaining a portion of a volumetric image that corresponds with a plane of the tomosynthesis image; and
comparing the portion of the volumetric image with the tomosynthesis image.

37. The method of claim 22, further comprising:
determine an additional digital tomosynthesis images using at least some of the plurality of images obtained while the radiation source is at the different positions along the arc path; and
outputting the digital tomosynthesis images and the additional digital tomosynthesis image for display in a form of a video.

38. The method of claim 22, wherein the arc path is rectilinear with a corresponding infinite arc radius.

39. An imaging system, comprising:
a radiation source;
a positioner configured to rotate the radiation source along an arc path at a rate that is a equal to or less than $R_{max}$, $R_{max}$ being calculated from $\alpha$ and T, and being equal to $\alpha/T$, wherein the rate is a speed of rotation of the radiation source when the radiation source is rotating;
an imager in operative position relative to the radiation source, wherein the radiation source and the imager are configured to obtain a plurality of images while the radiation source is at different positions along the arc path; and
a processor configured to determine a digital tomosynthesis image using a subset of the plurality of images;
wherein $\alpha$ is an angular spacing between a subset of the images that belongs to a same bin, and T is a period of a physiological motion, wherein at least two images in the subset of the images belonging to the same bin correspond with two different respective positions of the radiation source; and
wherein the imaging system further comprises a processing module configured to calculate $R_{max}$ based on the angular spacing.

40. An imaging system, comprising:
a radiation source;
a positioner configured to rotate the radiation source along an arc path at a rate that is a equal to or less than $R_{max}$, $R_{max}$ being calculated from $\alpha$ and T, and being equal to $\alpha/T$, wherein the rate is a speed of rotation of the radiation source when the radiation source is rotating;
an imager in operative position relative to the radiation source, wherein the radiation source and the imager are configured to obtain a plurality of images while the radiation source is at different positions along the arc path; and
a processor configured to determine a digital tomosynthesis image using a subset of the plurality of images;
wherein $\alpha$ is an angular spacing between a subset of the images that belongs to a same bin, and T is a period of a physiological motion, wherein at least two images in the
subset of the images belonging to the same bin correspond with two different respective positions of the radiation source; and
wherein the imaging system further comprises a processing module configured to calculate $R_{max}$ based on the period of the physiological motion.

41. An imaging method, comprising:
generating a control signal to control a positioner to rotate a radiation source through an arc path at a rate that is less than or equal to $R_{max}$, $R_{max}$ being calculated from $\alpha$ and T using a processing unit, and being equal to $\alpha/T$, wherein the rate is a speed of rotation of the radiation source when the radiation source is rotating; and
obtaining a plurality of images that are generated using radiation from the radiation source while the radiation source is at different positions along the arc path; and
determining a digital tomosynthesis image using a subset of the plurality of images;
wherein $\alpha$ is an angular spacing between a subset of the images that belongs to a same bin, and T is a period of a physiological motion, wherein at least two images in the subset of the images belonging to the same bin correspond with two different respective positions of the radiation source; and
wherein the imaging method further comprises calculating $R_{max}$ based on the angular spacing.

42. An imaging method, comprising:
generating a control signal to control a positioner to rotate a radiation source through an arc path at a rate that is less than or equal to $R_{max}$, $R_{max}$ being calculated from $\alpha$ and T using a processing unit, and being equal to $\alpha/T$, wherein the rate is a speed of rotation of the radiation source when the radiation source is rotating; and obtaining a plurality of images that are generated using radiation from the radiation source while the radiation source is at different positions along the arc path; and determining a digital tomosynthesis image using a subset of the plurality of images;

wherein α is an angular spacing between a subset of the images that belongs to a same bin, and T is a period of a physiological motion, wherein at least two images in the subset of the images belonging to the same bin correspond with two different respective positions of the radiation source; and wherein the imaging method further comprises calculating $R_{max}$, based on the period of the physiological motion.

43. An imaging system, comprising:

a processing module configured to calculate a maximum rate of rotation based on an angular spacing between two images to be formed;

a radiation source;

a positioner configured to rotate the radiation source along an arc path at a rate that is less than 0.25 degree/second, wherein the rate is a speed of rotation of the radiation source when the radiation source is rotating; and an imager in operative position relative to the radiation source, wherein the radiation source and the imager are configured to obtain a plurality of images that includes the two images while the radiation source is at different positions along the arc path.

44. An imaging system, comprising:

a radiation source;

a positioner configured to rotate the radiation source along an arc path at a rate that is less than 0.25 degree/second, wherein the rate is a speed of rotation of the radiation source when the radiation source is rotating;

an imager in operative position relative to the radiation source, wherein the radiation source and the imager are configured to obtain a plurality of images while the radiation source is at different positions along the arc path; and a processing module configured to calculate a maximum rate of rotation based on a period of a physiological motion.

45. An imaging method, comprising:

calculating a maximum rate of rotation for a radiation source based on an angular spacing between images that belongs to a same bin;

generating a control signal to control a positioner to rotate the radiation source through an arc path at a rate that is less than 0.25 degree/second, wherein the rate is a speed of rotation of the radiation source when the radiation source is rotating; and obtaining the images that are generated using radiation from the radiation source while the radiation source is at different positions along the arc path.

46. An imaging method, comprising:

calculating a maximum rate of rotation for a radiation source based on a period of physiological motion;

generating a control signal to control a positioner to rotate the radiation source through an arc path at a rate that is less than 0.25 degree/second, wherein the rate is a speed of rotation of the radiation source when the radiation source is rotating; and obtaining a plurality of images that are generated using radiation from the radiation source while the radiation source is at different positions along the arc path.

* * * * *